(12) United States Patent
Neumann (10) Patent No.: US 11,526,555 B2
(45) Date of Patent: Dec. 13, 2022

(54) METHOD AND SYSTEM FOR DETERMINING USER TASTE CHANGES USING A PLURALITY OF BIOLOGICAL EXTRACTION DATA

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 202 days.

(21) Appl. No.: 16/890,748

(22) Filed: Jun. 2, 2020

(65) Prior Publication Data

US 2021/0374182 A1 Dec. 2, 2021

(51) Int. Cl.
*G06F 16/9035* (2019.01)
*G16H 10/60* (2018.01)
*G16B 20/50* (2019.01)
*G06N 20/00* (2019.01)

(52) U.S. Cl.
CPC ......... *G06F 16/9035* (2019.01); *G06N 20/00* (2019.01); *G16B 20/50* (2019.02); *G16H 10/60* (2018.01)

(58) Field of Classification Search
None
See application file for complete search history.

(56) References Cited

U.S. PATENT DOCUMENTS

| | | |
|---|---|---|
| 7,541,548 B1 | 6/2009 | Sze |
| 8,731,970 B2 | 5/2014 | Hermann et al. |
| 9,349,297 B1 | 5/2016 | Ortiz et al. |
| 9,528,972 B2 | 12/2016 | Minvielle |
| 10,496,798 B2 | 12/2019 | Wilkinson |
| 2004/0191862 A1* | 9/2004 | Zoller ............ G01N 33/5008 435/69.1 |
| 2006/0199155 A1 | 9/2006 | Mosher |
| 2008/0086374 A1 | 4/2008 | Aitken |
| 2008/0145842 A1* | 6/2008 | Takao ............ C12Q 1/6883 435/6.12 |
| 2010/0136508 A1 | 6/2010 | Zekhtser |
| 2016/0225284 A1 | 8/2016 | Schoen |
| 2017/0193853 A1 | 7/2017 | Byron et al. |
| 2020/0074884 A1 | 3/2020 | Murdoch et al. |
| 2020/0098466 A1 | 3/2020 | Murdoch et al. |

OTHER PUBLICATIONS

Reed et al. The Journal of Neuroscience, 2004, 24(4), 938-946.*
Chen et al. Brain Research, 1325 (2010) 53-62.*
Fabris et al. Biogerontology 18:171-188, 2017.*
Im et al . Environ Earth Sci , 75:1120, 1-19, 2016.*
Kavakiotis et al. Computational and Structural Biotechnology Journal, 104-116, 2017.*
Bhide et al. "The Power of Profiling: How automated classification aids data governance". www.ibm.com/cloud/blog/power-profiling-automated-classification-aids-data-governance, Jan. 19, 2018.*
Moniruzzaman et al. NoSQL Database: New Era of Databases for Big data Analytics—Classification, Characteristics and Comparison International Journal of Database Theory and Application vol. 6, No. 4. 1-14, 2013.*

* cited by examiner

*Primary Examiner* — Michael L Borin
(74) *Attorney, Agent, or Firm* — Caldwell Intellectual Property Law (57) ABSTRACT

A system for determining user taste changes using a plurality of biological extraction data and artificial intelligence includes at least a computing device, wherein the computing device is designed and configured to receive, from a user, at least a first element of biological extraction data, calculate at least a first taste index of the user, wherein calculating further comprises training a first machine learning process as a function of training data correlating biological extraction data with taste indices, calculating the at least a first taste index as a function of the first machine learning process and the at least a first element of biological extraction data, generate a taste profile using the first taste index, and determine, using at least a second element of biological extraction data and a second machine learning process, at least a change in user taste profile.

16 Claims, 6 Drawing Sheets

METHOD AND SYSTEM FOR DETERMINING USER TASTE CHANGES USING A PLURALITY OF BIOLOGICAL EXTRACTION DATA

FIELD OF THE INVENTION

The present invention generally relates to the field of artificial intelligence. In particular, the present invention is directed to a method and system for determining user taste changes using a plurality of biological extraction data.

BACKGROUND

Systems that generate individual chemosensory profiles are often overloaded with data. Frequently, individual preferences are analyzed and assessed on a massive scale with little account for how references change over time. Worse, genetic variants among selections and individual likes and dislikes regarding taste are not considered.

SUMMARY OF THE DISCLOSURE

In an aspect, a system for determining user taste changes using a plurality of biological extraction data includes at least a computing device, wherein the computing device is designed and configured to receive, from a user, at least a first element of biological extraction data, calculate at least a first taste index of the user as a function of the at least a first element of biological extraction data, generate a taste profile using the first taste index, and determine, using at least a second element of biological extraction data and a second machine learning process, at least a change in user taste profile.

In another aspect, a method for determining user taste changes using a plurality of biological extraction data includes at least a computing device, wherein the computing device is designed and configured to receive, from a user, at least a first element of biological extraction data, calculate at least a first taste index of the user, wherein calculating further comprises training a machine learning process as a function of training data correlating biological extraction data with taste indices, calculating the at least a first taste index as a function of the machine learning process and the at least a first element of biological extraction data, generate a taste profile using the first taste index, and determine, using at least a second element of biological extraction data and a second machine learning process, at least a change in user taste profile.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to methods and systems, for determining user taste changes using a plurality of biological extraction data and artificial intelligence. In an embodiment, a computing device receives a user biological extraction data. A computing device uses a machine learning process and a plurality user biological extraction data to calculate a taste index. A computing device uses a machine learning model and at least a taste index to generate a taste profile of a user. A computing device using at least a second element of biological extraction data and a machine learning process, determines at least a change in user taste profile.

Figure 1:
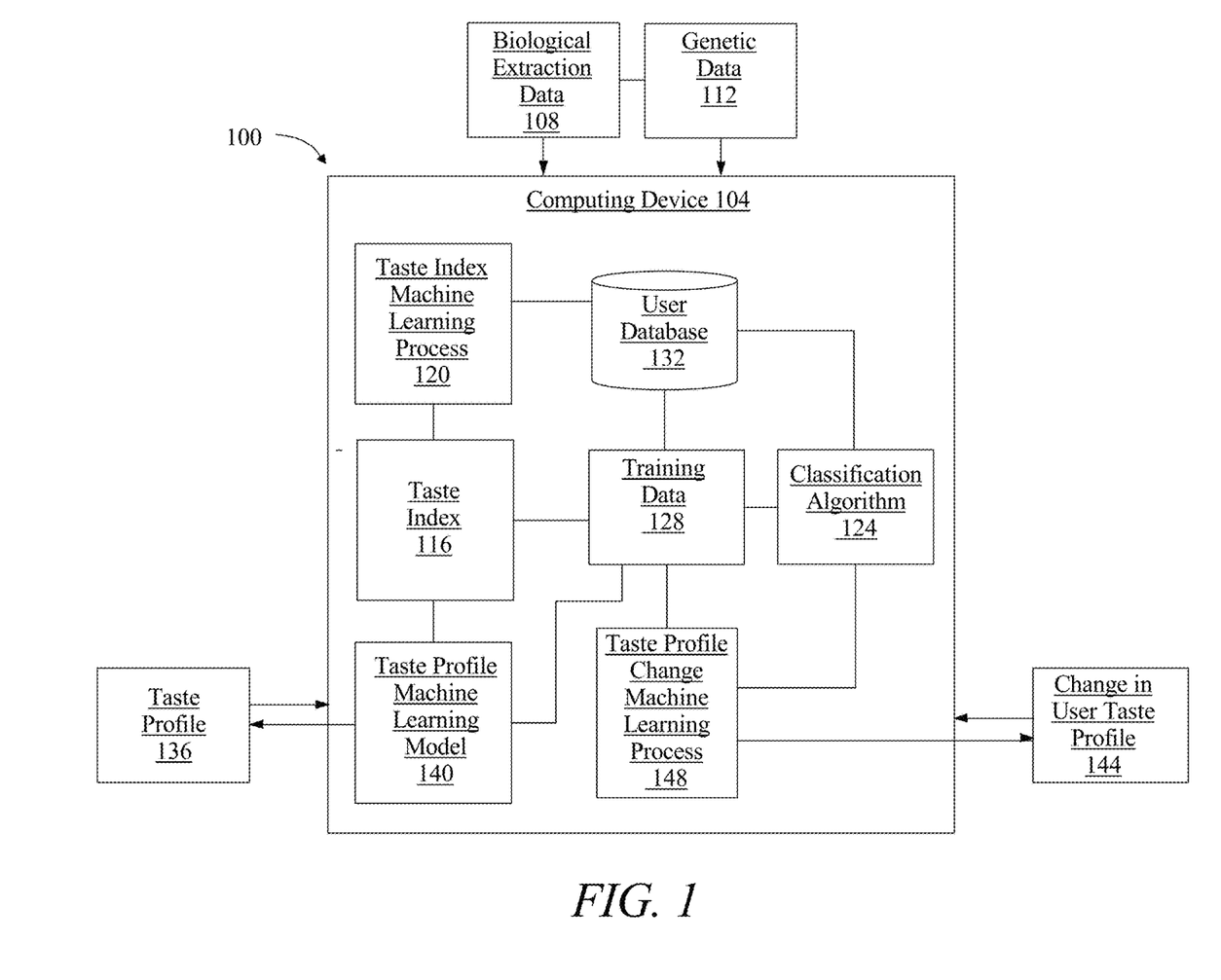
FIG. 1 is a block diagram of an exemplary embodiment of a system for determining user taste changes using a plurality of biological extraction data and artificial intelligence.

Referring now to FIG. 1, an exemplary embodiment of a system 100 for determining user taste changes using a plurality of biological extraction data and artificial intelligence is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently, or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device 104.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

In reference to FIG. 1, computing device 104 is designed and configured to receive, from a user, at least a first element of biological extraction 108 data. As used in this disclosure, "biological extraction," may refer to an element of user data corresponding to a category, including without limitation, microbiome analysis, blood test results, gut wall and food sensitivity analysis, toxicity report, medical history, biomarker, genetic or epigenetic indication, or any chemical, biological, or physiological markers of data of a user, including for instance, and without limitation, as described in U.S. Nonprovisional application Ser. No. 16/865,740, filed on May 4, 2020, and entitled "METHODS AND SYSTEMS FOR SYSTEM FOR NUTRITIONAL RECOMMENDATION USING ARTIFICIAL INTELLIGENCE ANALYSIS FOR IMMUNE IMPACTS," the entirety of which is incorporated herein by reference. As a non-limiting example, a plurality of user biological extraction 108 data may refer to at least any two elements of data of biological extraction 108, wherein at least an element of biological extraction 108 data corresponds to genetic data.

With continued reference to FIG. 1, at least a first element of biological extraction 108 data includes genetic data 112. As used in this disclosure, "genetic data," refers to at least an element of data that describes any genetic material including nucleic acids such as DNA and RNA, which may correspond to genetic elements of a user including coding regions (genes), non-coding regions such as promoters, enhancers, transposons, genome-integrated viral DNA, and the presence of structural RNA, such as tRNAs, miRNAs and other RNA types, and/or any analysis thereof; analysis may refer to detecting the presence of, enumeration of, and/or determining the sequence of a nucleic acid and/or stretch of nucleic acid. Genetic data 112 may be obtained from at least a user physical sample. As described here, "physical sample," is a biological user sample including blood, urine, feces, hair, saliva, skin, interstitial fluid, biopsy, or any other physical biological sample that genetic information may be obtained. Genetic data 112 may be stored and/or retrieved from a database, as described below. It will be understood by those skilled in the art, after reviewing the disclosure in its entirety, the various data that are represented by a genetic analysis, and the various ways in which genetic data 112 may be stored and/or retrieved for the purposes described herein.

Still referring to FIG. 1, computing device 104 is configured to calculate, using the at least a first element of biological extraction 108 data, at least a first taste index 116 of the user. As used in this disclosure, "taste index," refers to any mathematical, causative, correlated, proportional, heuristic, and/or any other relationship between two elements of data that is a measure of chemosensory phenomenon as it relates to the sense of taste. A taste index 116 may be a matrix, vector, function, and/or numerical value that measures at least an aspect of taste. For instance, in non-limiting illustrative examples, a taste index 116 may be a function that describes a relationship between the affinity for the level of sweetness a user may taste based on the expression of "sweetness-sensing genes" such as genes involved in the cellular signaling of molecules associated with "sweetness" such as monosaccharides such as glucose, fructose, galactose, disaccharides such as sucrose, lactose, maltose, polysaccharides such as glycogen, cellulose, chitin, artificial sweeteners such as saccharin, aspartame, sucralose, and/or their metabolites. In further non-limiting illustrative examples, a taste index 116 may be calculated form an element of biological extraction 108, such as an element of genetic data 112, and an element of data retrieved from a database, as described below. A taste index 116 may include smell, including any power of perceiving odors or scents by means of the organs in the nose. In further non-limiting illustrative examples, a taste index 116 may be calculated via a mathematical operation, for instance and without limitation by addition of variables, from two elements of biological extraction 108, wherein for instance without limitation a first element is genetic data 112, and a second element is a known medical condition. In non-limiting examples, one or more elements of data used by a computing device for calculating a taste index 116 may be retrieved from a database. In further non-limiting examples, a query may be used to search for a particular element of data as needed to calculate a taste index 116. In non-limiting illustrative examples, a particular element of data queried from a database may be searched for by use of a classifier, as described in further detail below.

Continuing in reference to FIG. 1, at least a taste index may be calculated using an index machine learning process 120. Index machine learning process 120 may include at least a supervised machine learning algorithm. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include an element of biological extraction 108 data as described above as inputs, taste indices as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

Supervised machine learning processes may include classification algorithms 124, defined as processes whereby at least a computing device 104 derives, from training data, a model for sorting inputs into categories or bins of data. Classification may be performed using, without limitation, linear classifiers such as without limitation logistic regression and/or naive Bayes classifiers, regression algorithms, nearest neighbor classifiers, support vector machines, decision trees, boosted trees, random forest classifiers, and/or neural network-based classifiers, such as supervised neural net algorithms. Supervised machine learning processes may include, without limitation, machine learning processes as described in U.S. Nonprovisional application Ser. No. 16/520,835, filed on Jul. 3, 2019, and entitled "METHODS AND SYSTEMS FOR ACHIEVING VIBRANT CONSTITUTION BASED ON USER INPUTS," the entirety of which is incorporated herein by reference.

Continuing in reference to FIG. 1, "training data," as used herein, is data containing correlations that a machine learning process may use to model relationships between two or more categories of data elements. For instance, and without limitation, training data 128 may include a plurality of data entries, each entry representing a set of data elements that were recorded, received, and/or generated together; data elements may be correlated by shared existence in a given data entry, by proximity in a given data entry, or the like. Multiple data entries in training data 128 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 128 according to various correlations; correlations may indicate causative and/or predictive links between categories of data elements, which may be modeled as relationships such as mathematical relationships by machine learning processes as described in further detail below. Training data 128 may be formatted and/or organized by categories of data elements, for instance by associating data elements with one or more descriptors corresponding to categories of data elements. As a non-limiting example, training data 128 may include data entered in standardized forms by persons or processes, such that entry of a given data element in a given field in a form may be mapped to one or more descriptors of categories. Elements in training data 128 may be linked to descriptors of categories by tags, tokens, or other data elements; for instance, and without limitation, training data 128 may be provided in fixed-length formats, formats linking positions of data to categories such as comma-separated value (CSV) formats and/or self-describing formats such as extensible markup language (XML), enabling processes or devices to detect categories of data.

Alternatively or additionally, training data 128 may include one or more elements that are not categorized; that is, training data 128 may not be formatted or contain descriptors for some elements of data. Machine learning algorithms and/or other processes may sort training data 128 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 128 to be made applicable for two or more distinct machine learning algorithms as described in further detail below. Training data 128 used by computing device 104 may correlate any input data as described in this disclosure to any output data as described in this disclosure. Training data may contain entries, each of which correlates a machine learning process input to a machine learning process output, for instance without limitation, one or more elements of biological extraction data to a taste index. Training data may be obtained from previous iterations of machine-learning processes, user inputs, and/or expert inputs.

Still referring to FIG. 1, computing device 104 may calculate at least a first taste index of a user using a taste index machine learning process 120 and at least an element of biological extraction 108 data to generate, as an output, at least a taste index 116 of a user of a plurality of taste indices. Computing device 104 may generate a taste index by training index machine learning process 120 as a function of training data correlating biological extraction data with taste indices, and calculating the at least a first taste index as a function of the first machine learning process and the at least a first element of biological extraction data. Machine learning process, and/or a machine learning model produced thereby, may be trained by at least a computing device 104 using training data, which may be retrieved from a database, as described below, as it correlates to user biological extraction 108 data. Machine learning process may accomplish this by using genetic data 112 as it relates to at least a biological extraction 108 and a calculated chemosensory value as it relates to other users.

Figure 2:
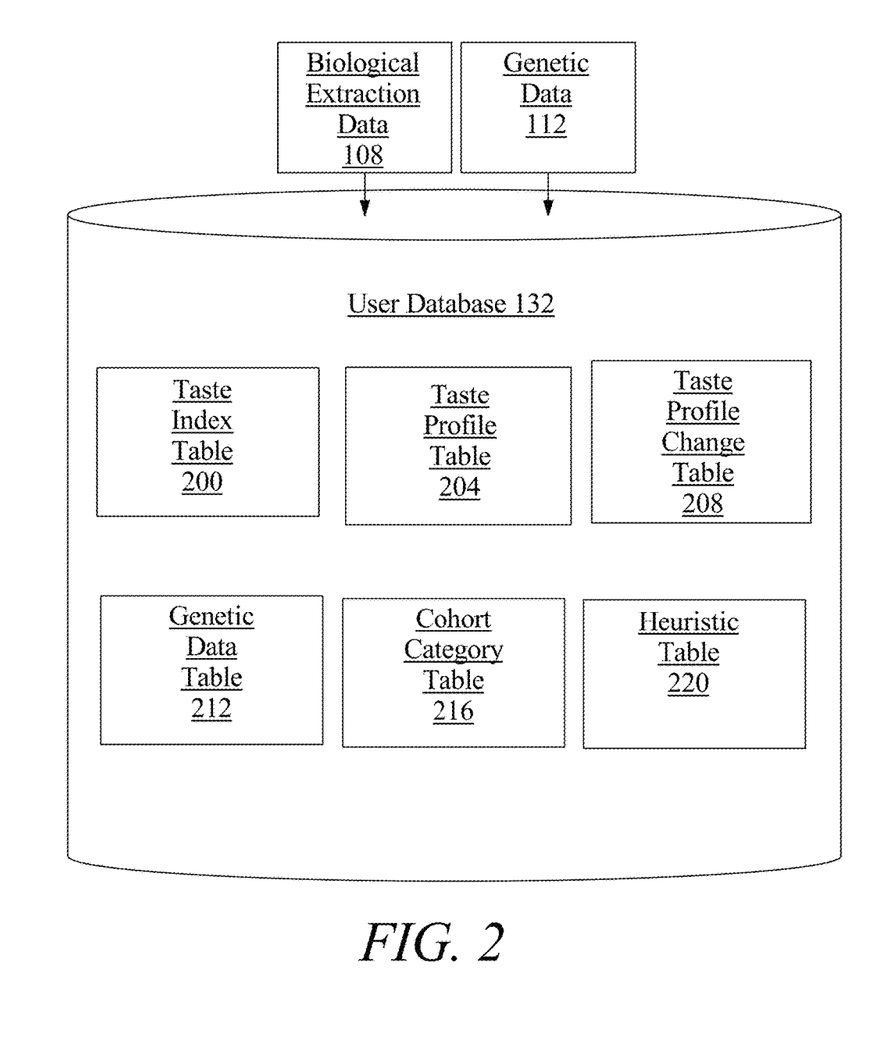
FIG. 2 is a block diagram of an exemplary embodiment of a user database.

Referring now to FIG. 2, a non-limiting exemplary embodiment of a database is illustrated. Database may refer to a "user database" which at least a computing device 104 may, alternatively or additionally, store and/or retrieve data from a taste index table 200, taste index table 204, and taste profile change table 208. Determinations by a machine learning process may also be stored and/or retrieved from the user database 132, for instance in non-limiting examples a classifier. As a non-limiting example, user database 132 may organize data according to one or more taste profile tables 208. One or more database tables may be linked to one another by, for instance in a non-limiting example, common column values. For instance, a common column between two tables of user database 132 may include an identifier of a submission, such as a form entry, textual submission, research paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which data from one or more tables may be linked and/or related to data in one or more other tables.

Still referring to FIG. 2, in a non-limiting embodiment, one or more tables of a user database 132 may include, as a non-limiting example, a genetic data table 212, which may include genetic analyses for use in predicting taste of a user and/or correlating biological extraction 108 data, entries indicating degrees of relevance to and/or efficacy in predicting taste of a user, and/or other elements of data computing device 104 and/or system 100 may use to determine usefulness and/or relevance of biological extraction 108 in determining taste index 116, taste profile, and/or changes in taste profile as described in this disclosure. One or more tables may include a genetic data table 212, which may correlate genetic data and/or combinations thereof to one or more measures of taste; taste index table 200, which may contain a plurality of entries associating at least an element of biological extraction 108 data with a relationship to taste. One or more tables may include, without limitation, a taste index table 204 which may contain one or more inputs identifying one or more categories of data, for instance a palatable range of capsaicin. One or more tables may include, without limitation, a change in taste index table 204, which may contain one or more inputs identifying one or more categories of data, for instance change in taste over a year period. One or more tables may include, without limitation, a cohort category table 216 which may contain one or more inputs identifying one or more categories of data, for instance demographic data, medical history data, physiological data, or the like, with regard to which users having matching or similar data may be expected to have similar taste indices and/or taste profiles as a result of genetic elements and/or other biological extraction 108 data. One or more tables may include, without limitation, a heuristic table 220, which may include one or more inputs describing potential mathematical relationships between at least an element of biological extraction 108 data and taste index 116, taste profile, and/or change in taste profile, as described in further detail below.

Figure 3:
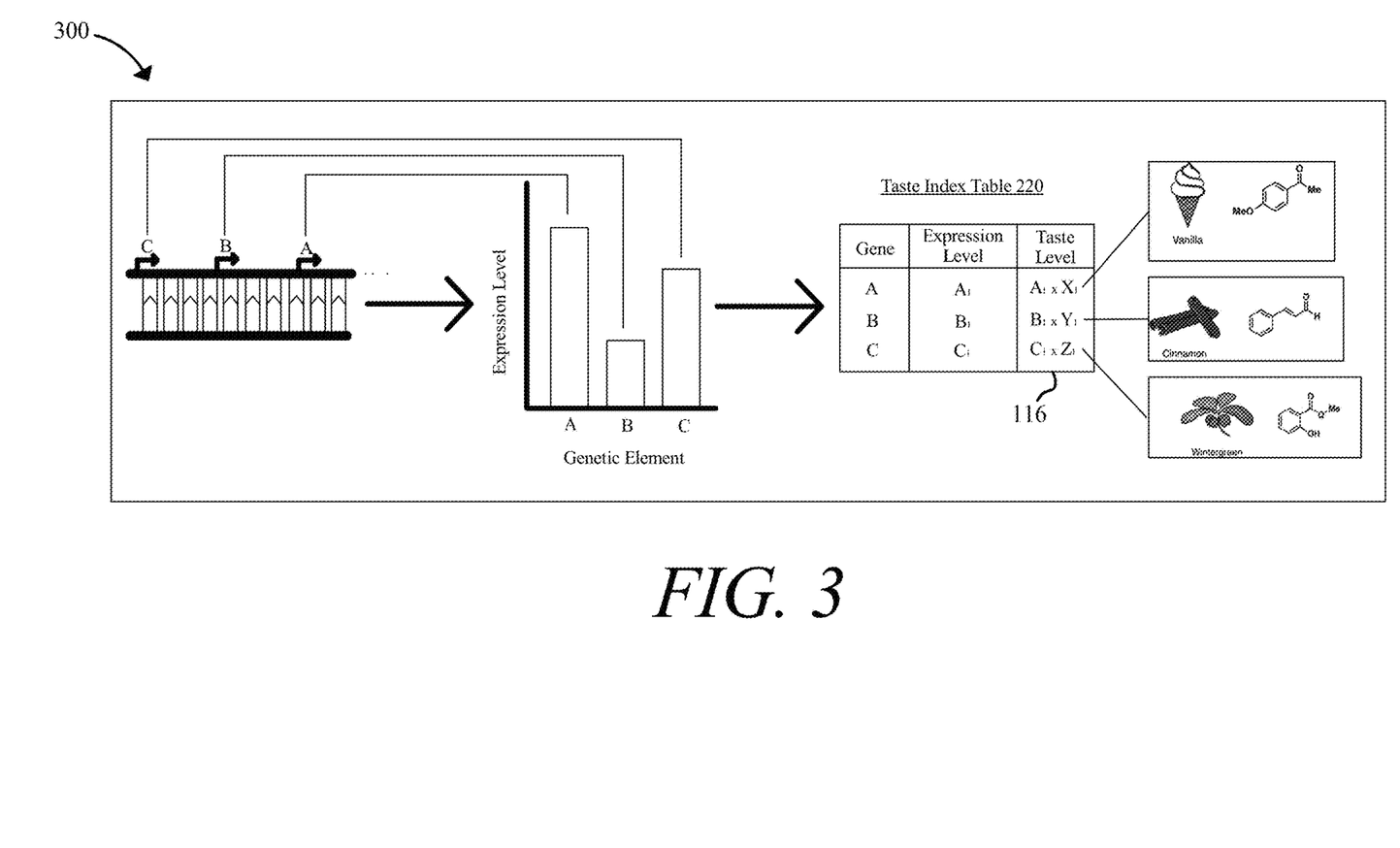
FIG. 3 is a schematic diagram describing an exemplary embodiment of calculating taste indices.

Referring now to FIG. 3, schematic diagram 300 of a process for calculating a taste index 116 and/or plurality of taste indices may include determining correlations between at least an element of biological extraction 108 data and at least an element of data retrieved from a database, where determination may be accomplished using database queries and/or machine-learning processes as described above. In non-limiting illustrative examples, a taste index 116 may be a function of a user's expression level of a variety of taste-sensing genes that produce taste-sensing proteins in the tongue, for instance, T2Rs, T1Rs, ENaC, GLUT4, and SGLT1, and a database value that links the protein level from these genes to their functionality in the tongue. In further non-limiting examples, a taste index 116 and/or a plurality of taste indices may be a function that relates the expression level of the TAS2Rs and TAS1Rs G-protein coupled receptors in the tongue to a correlated amount of sweetness flavor that is palatable to a user for a variety of flavors, for instance vanilla, cinnamon, and wintergreen. A taste index machine learning process 120 may accept inputs of an element of biological extraction 108 and an element of data retrieved from a database to calculate a function describing a relationship between the two, to output a taste index 116 of a plurality of taste indices.

Referring again to FIG. 1, generating a taste profile 136 may include generating a taste classifier that associates taste indices 116 with taste profiles 136; and generating the first taste profile 136 as a function of the first taste index 116 and/or plurality of taste indices 116. A "taste profile," as described in this disclosure, refers to a user's chemosensory ability as it relates to one or more elements of data of sensing a variety of flavors, such as sweet, sour, salty, bitter, savory (umami), fatty, alkaline, acidic, metallic, and water-like; user preference for texture, temperature, and consistency in taste; information extracted from biological extraction 108 data about pain-sensing neurons, the amount, integrity, and/or functionality in the tongue for tasting and/or sensing "spiciness and/or hotness;" information extracted from biological extraction 108 data that includes the amount, integrity, and/or functionality in the mouth, throat, sinus, and tongue, for mucous membranes, taste papillae, and taste buds, including nerve fibers, basal cells, supporting cells, and taste hairs. A taste profile 136 may include smell, including any power of perceiving odors or scents by means of the organs in the nose. A taste profile 136 may be calculated by a computing device 104 using any mathematical operation, for instance without limitation via addition of values of taste indices 116. Alternatively or additionally, a taste profile 136 may be generate as an output of a machine learning process. A machine learning process may be trained with training data to generate a machine learning model, as described in further detail below. Machine learning model may be trained using training data that includes at least a taste index 116 of a plurality of taste indices and a correlation thereof to one or more elements of a taste profile may be identified by use of taste classifier output as described above. The model may be used, along with taste index inputs, to generate a taste profile 136. In non-limiting examples, a taste profile machine learning model 140 may input two taste indices, a first that describes a user's sensitivity to sweetness, and a second that describes a user's sensitivity to bitterness, and output a taste profile 136 that summarizes the total user's taste sensitivity, which may for instance without limitation determine a user's palatability for cacao content in chocolate, or predict which types of wine a user may find palatable. Alternatively or additionally, a taste profile 136 may refer to an output from a machine learning process using a taste profile machine learning model 140 summarizing values calculated from a plurality of taste indices as it may relate to food items and/or meals. A classifier, such as a taste classifier produced by a classification algorithm 124, may be used to generate a taste profile. A taste classifier may be trained with using training data, which may be selected using a second classifier, such as a user classifier; where user classifier may be used to identify training data corresponding to users matching user according to user classifier. For instance, user classifier may be used to classify user to a category of users. Computing device may then select training data matching the category of users and train the taste classifier using the selected training data.

Figure 4:
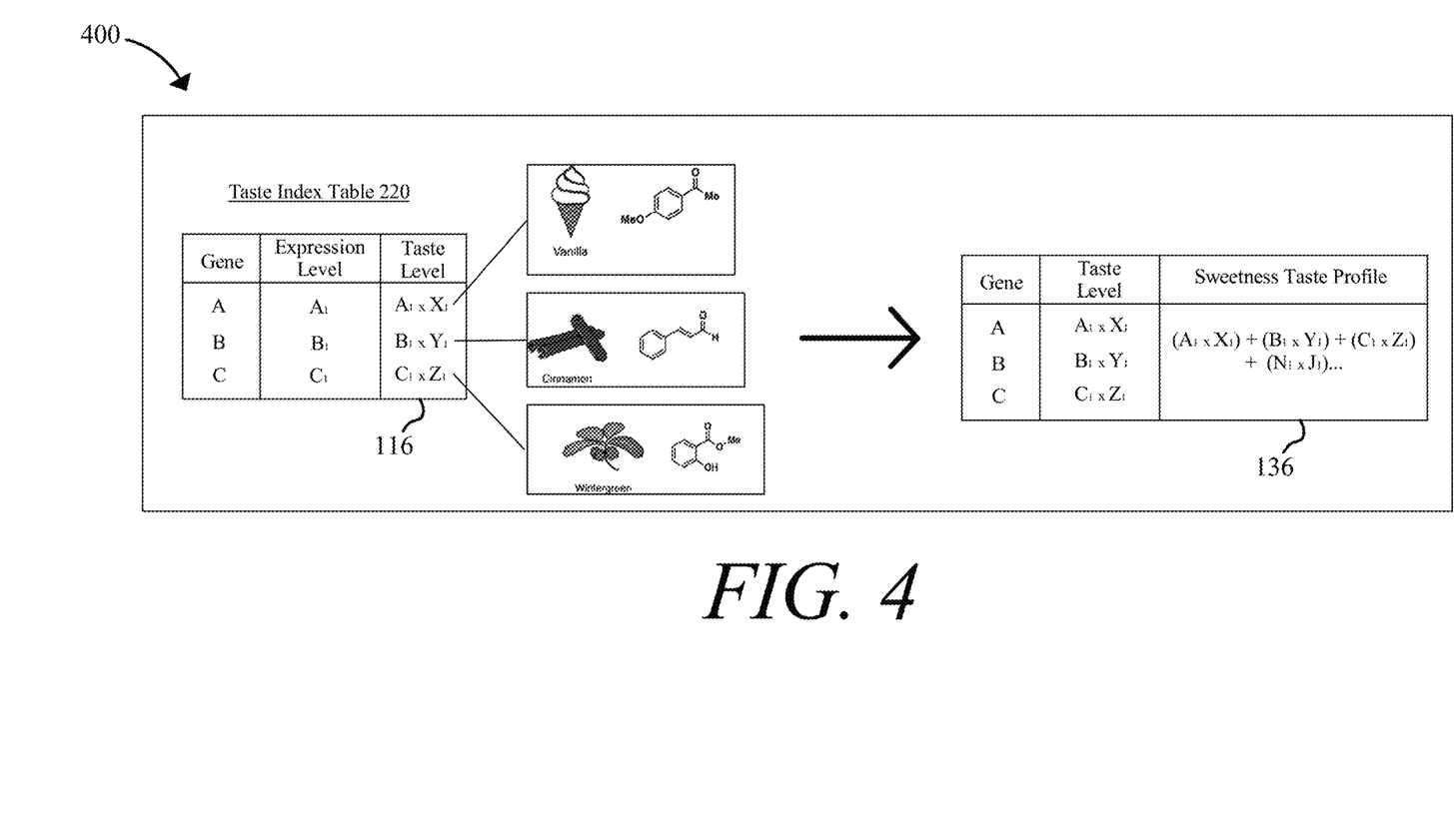
FIG. 4 is a schematic diagram describing an exemplary embodiment of generating a taste profile.

Referring now to FIG. 4, a schematic diagram 400 illustrating exemplary processes of generating a taste profile 136 from a plurality of taste indices 116 is illustrated. In exemplary illustrative embodiments, a taste profile machine learning model 140 may be trained with training data that may be a plurality of taste indices relating to sweetness to generate a taste profile 136 that is a function, vector, table, or any numerical value relating to the overall level of sweetness a user may be able to taste, as previously described. In non-limiting illustrative embodiments, taste indices 116 may be stored and/or retrieved from a taste index table 220 of a user database 132 for use as training data.

In non-limiting illustrative examples, a classifier may refer to a subset of user data that correlates biological extraction 108, database entries, taste indices, and/or taste profiles 128 to a taste profile 136 that may be used to train a machine learning model to produce subsequent taste profiles 128. Alternatively or additionally, a classifier may be assigned, to an explicit category or subset of data of an output of a machine learning model. For instance, without limitation, subsets of a taste profile machine learning model 140 output may contain data useful to subsequent machine learning models. A classifier assigned to input and/or output of a machine learning model may be stored and/or retrieved by a computing device 104, without limitation, such as from a user database 132.

Continuing in reference to FIG. 1, a computing device 104 may determine a change in user taste profile 144 using at least a second element of biological extraction data as a function of two distinct taste profiles 128. In non-limiting illustrative embodiments, a change in user taste profile 144 may include at least two distinct taste profiles 128 as an input into a taste profile change machine learning process 148 to output a change in taste profiles, as previously described. A taste index machine learning process 120 may input a plurality of biological extraction 108 and a database entry and output at least a taste index 116 of a plurality of taste indices. A taste profile machine learning model 140 may then be trained using training data 128 that is a plurality of taste profiles 128 to output a taste profile 136 that summarizes how a user's biological extraction 108 relates to taste. A taste profile change machine learning process 148 may input at least two distinct taste profiles 128, of a plurality of taste profiles 128, and output a change in user taste profile 144 that is at least a difference between the input taste profiles 128. In non-limiting illustrative examples, the plurality of taste profiles 128 may be of the first user or a first user and at least a second user. In non-limiting illustrative examples, a change in user taste profile 144 may show no difference. Taste profile change machine learning process 148 may be the same as taste index machine learning process 120. Taste profile change machine learning process 148 may input taste profiles 128 from a database, for instance without limitation a taste index table 204 in a user database 132. Change in user taste profile 144 may be stored and/or retrieved from a database, as described above.

Continuing in reference to FIG. 1, determining a change in user taste profile 144 may include using at least a second element of biological extraction 108 data wherein a second element of biological extraction 108 is more recent than a first element of biological extraction 108 data. As used in this disclosure, "more recent," may mean for instance and without limitation, at least a second element of biological extraction data was sampled and/or extracted more recently than a first element of biological extraction data. In non-limiting illustrative embodiments, change in user taste profile 144 for a first user may be calculated between two distinct taste profiles 128, wherein change in user taste profile 144 may be attributed to a change in biological extraction 108 data for a first user over time. In non-limiting illustrative examples, a second taste profile 136 may summarize taste from biological extraction 108 data prior to a first taste profile 136. In further non-limiting illustrative examples, a change in user taste profile 136 may be determined between two or more distinct taste profiles 128, wherein one taste profile 136 is from a first user and a second taste profile 136 is from a second user of a plurality of other users. Change in user taste profile 136 may be calculated between any number of taste profiles 128 from any number of users, over any period of time, for instance without limitation, monthly changes in taste of a subset of users, over the course of a year. In non-limiting illustrative embodiments, a change in user taste profile 144 may use a classifier denoting a subset of users. In non-limiting illustrative examples, change in user taste profile 144 may be determined for a classified subset of users who have been recently diagnosed with cancer and undergo similar chemotherapy regimens. In further non-limiting examples, change in user taste profile 144 may be determined to describe how the chemotherapy affects sense of taste in this subset, for instance if users are developing a metallic taste when drinking water. In further non-limiting examples, change in user taste profile 144 would determine a difference as a function of a first taste profile 136 prior to cancer treatment and a second taste profile 140 after cancer treatment has begun. In an embodiment, a change in user taste profile 144 may be calculated based on historical consumption of any foods, beverages, meals, and/or snacks intended for consumption by a human being. A change in user taste profile 144 may be calculated based on a user's preferences regarding the consumption of any foods, beverages, meals, and/or snacks intended for consumption by a human being. Information pertaining to user preferences and/or historical consumption of such items may be stored within user database and utilized in one or more machine-learning processes, including any machine-learning process as described herein.

Continuing in reference to FIG. 1, determining a change in user taste profile 144 may include calculating a difference between at least a plurality of taste profiles 128 to at least an element of biological extraction 108. A taste profile change machine learning process 148 used to calculate a change in user taste profile 144 may input any number of taste profiles 128 determine a change. Change in user taste profile 144 may be changes in taste and/or changes in biological extraction 108 data. In non-limiting illustrative examples, a change in user taste profile 144 may be no difference in user taste, but a change in biological extraction 108, wherein two distinct biological extractions 108 result in similar taste profiles 128. Change in taste profile 136 may be an identification of a difference in the biological extraction 108 of a plurality of taste profiles 128. In non-limiting illustrative examples, change in taste profile 136 may represent outputs of biological extraction 108 difference such as without limitation, a diagnosis, epigenetic differences, differences in demographics, or the like.

Continuing in reference to FIG. 1, determining a change in user taste profile 144 may include a detecting a correlation between at least a genetic element of a user and a taste measurement. A taste profile change machine learning process 148 may output a change in user taste profile 144 that is a change in at least a taste measurement as it relates to a change in a genetic element of a user, as described above. A taste measurement is a taste index 116, such as a numerical value that describes a change between two or more taste profiles 128. In non-limiting examples, a taste measurement may be a percent change in palatability of sweetness in a user, or for instance without limitation, a gram sugar content per serving change in user taste. Change in user taste profile 144 may include without limitation a numerical change in taste mapped, connected, and/or otherwise linked to a change in a genetic element of a user. In non-limiting illustrative examples, a change in a genetic element may correspond to no change detected. In further non-limiting illustrative examples, a change in genetic element may not correspond to a change in user taste, which may be useful information in determining a change in taste attributed to biological extraction 108 other than a genetic element. In non-limiting illustrative examples, a machine learning model may be generated with training data 128 from a subset of biological extraction 108 data identified by, or described by a classifier, to determine a change in user taste profile 144 that may not be genetic. This may be performed, for instance without limitation, by training data 128 from a plurality of biological extraction 108 data, taste indices 116, taste profiles 128, and/or other changes in user taste.

Continuing in reference to FIG. 1, correlation may include use of a classifier that limits training data for a machine learning process, wherein the machine learning process is used to determine a change in user taste profile. Training data that includes at least a taste profile 136 of a plurality of taste profiles 136 may be identified by use of a classifier output from a machine learning process, as described above. In non-limiting illustrative examples, generating a change in user taste profile may include using a classifier that describes a plurality of biological extraction data entries. Alternatively or additionally, a subset of data for instance without limitation a plurality of taste indices may be identified by a classifier and may be used with a second machine learning process to generate a change in user taste profile. A second machine learning process generating an output that is at least a change in user taste profile may use a machine learning model trained by data identified by at least a classifier.

Figure 5:
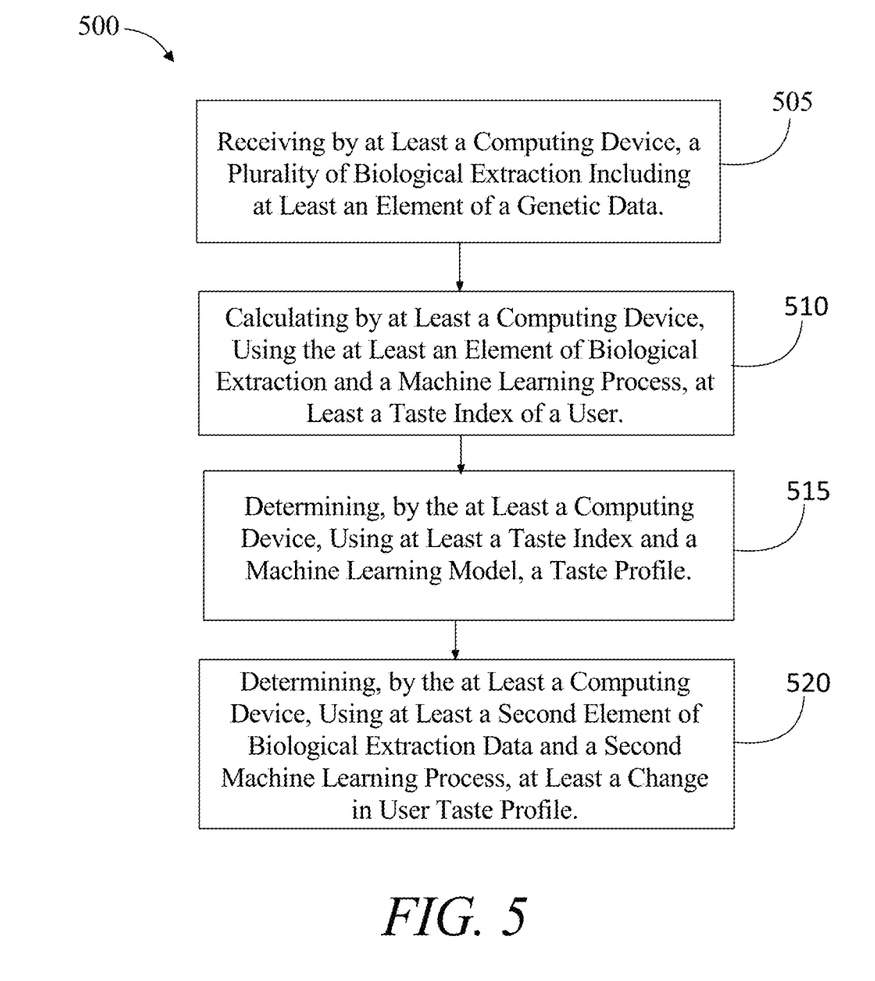
FIG. 5 is a flowchart describing an exemplary embodiment of a method using the system of the invention.

Referring now to FIG. 5, an exemplary embodiment of a method 500 of determining a change in user taste profile 144 using a plurality of biological extraction 108 user data and artificial intelligence. At step 505, method includes receiving by the at least a computing device 104, a plurality of biological extraction 108 including at least an element of genetic data; this may be implemented, without limitation, as described above in reference to FIGS. 1-4. It will be understood by those skilled in the art, after reviewing the disclosure in its entirety, the various ways user-reported data may be input in a computing device 104 and the various ways outputs may be displayed by a computing device 104 to a user for all steps described above.

Continuing in reference to FIG. 5, at step 510, method 500 includes calculating by the at least a computing device 104 using the at least an element of biological extraction 108 data and a taste index machine learning process 120, at least a taste index 116 of the user; this may be implemented, without limitation, as described above in reference to FIGS. 1-4.

Continuing in reference to FIG. 3, at step 515, method 500 includes determining, by the at least a computing device 104 using at least a taste index 116 and a machine learning model, a taste profile 136; this may be implemented, without limitation, as described above in reference to FIGS. 1-4. Generating a taste profile may include using a classifier that associates at least a taste index of a plurality of taste indices with a taste profile, generating a first taste profile as a function of at least a first taste index. Classifier for generating a taste profile further comprises using a classifier that limits training data for a first machine learning process. Generating a taste profile may include calculating a second taste index as a function of the second element of biological extraction, and then may include generating a classifier that associates a plurality of taste indices with a taste profile.

Continuing in reference to FIG. 5, at step 520, method 500 includes determining, using at least a second element of a biological extraction 108 data and a taste profile change machine learning process 148, at least a change in user taste profile 144; this may be implemented, without limitation, as described above in reference to FIGS. 1-4. It will be understood by those skilled in the art, after reviewing the disclosure in its entirety, the various ways data may be input in a computing device 104 and the various ways outputs may be displayed by a computing device 104 to a user for all steps described above. Determining a change in user taste profile may include generating a second taste profile and determining the change in user taste profile as a function of the first taste profile and the second taste profile. Generating a second taste profile may include receiving a second element of biological extraction, wherein a second element of biological extraction is more recent than a first element of biological extraction. Determining a change in user taste profile may include calculating a difference between the first taste profile and the second taste profile. Change in user taste profile may include a correlation between at least a genetic element of a user and a taste measurement. Generating a correlation between at least a genetic element of a user and a taste measurement may include using a classifier that limits training data for a machine learning process, wherein a machine learning process is used to determine a change in user taste profile.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM"

device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
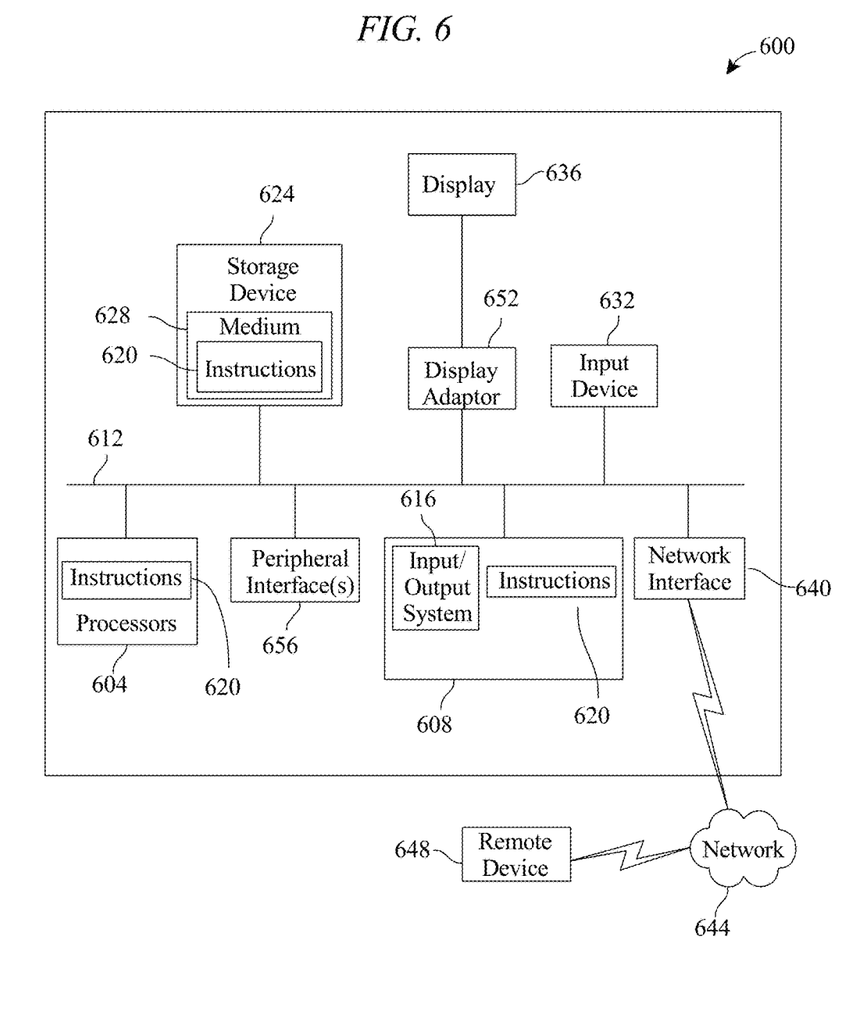
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for determining user taste changes using a plurality of biological extraction data, the system comprising at least a computing device, wherein the at least a computing device is designed and configured to:
   receive, at least a first element of biological extraction data;
   train, iteratively, a first machine-learning model using first training data correlating biological extraction data with database taste indices, wherein the first training data comprises information obtained from previous iterations of the first machine-learning model;
   calculate at least a first taste index of a user utilizing the first machine-learning model, wherein the first machine-learning model receives the at least a first element of biological extraction data as input and outputs the first taste index of the user, wherein the at least a first element of biological extraction data comprises genetic data, and wherein the first taste index comprises a relationship between two elements of data that is a measure of chemosensory phenomenon as it relates to a sense of taste;
   generate a taste profile using the first taste index, wherein generating a taste profile further comprises:
      training a second machine-learning model using second training data correlating database taste indices with taste profile data; and
      generating, using the second machine-learning model, the taste profile, wherein the second machine-learning model receives the first taste index as input and outputs the taste profile of the user;
   determine, a change in user taste profile, using at least a second element of biological extraction data as a function of two distinct taste profiles, wherein the second element of biological extraction data is more recent than the first element of biological extraction data; and
   offer at least a diagnosis to the user based on the change in the user taste profile.

2. The system of claim 1, wherein generating a taste profile further comprises:
   classifying the user to a category of users as a function of a user classifier;
   selecting a third training data matching the category of users; and
   training a taste classifier using the selected third training data.

3. The system of claim 1, wherein determining a change in user taste profile further comprises generating a second taste profile and determining the change in user taste profile as a function of the first taste profile and the second taste profile.

4. The system of claim 3, wherein generating the second taste profile further comprises receiving the second element of biological extraction.

5. The system of claim 4, wherein generating a taste profile further comprises:
   calculating a second taste index as a function of the second element of biological extraction data; and
   generating the second taste profile as a function of the second taste index.

6. The system of claim 5, wherein determining a change in user taste profile further comprises calculating a difference between the first taste profile and the second taste profile.

7. The system of claim 6, wherein the change in user taste profile further comprises a correlation between at least a genetic element of a user and a taste measurement.

8. The system of claim 7, wherein the correlation further comprises a correlation determined using a classifier that limits training data for a machine learning process.

9. A method of determining user taste changes using a plurality of biological extraction data, the method comprising:
   receiving, by a computing device, at least a first element of biological extraction data;
   training, iteratively, by the computing device, a first machine-learning model using first training data correlating biological extraction data with database taste indices, wherein the first training data comprises information obtained from previous iterations of the first machine-learning model;
   calculating, by the computing device, at least a first taste index of a user utilizing the first machine-learning model, wherein the first machine-learning model receives the at least a first element of biological extraction data as input and outputs the first taste index of the user, wherein the at least a first element of biological extraction data comprises genetic data, and wherein the first taste index comprises a relationship between two elements of data that is a measure of chemosensory phenomenon as it relates to a sense of taste;

generating, by the computing device, a taste profile using the first taste index, wherein generating a taste profile further comprises:

training a second machine-learning model using second training data correlating database taste indices with taste profile data; and generating, using the second machine-learning model, the taste profile, wherein the second machine-learning model receives the first taste index as input and outputs the taste profile of the user;

determining, by the computing device, a change in user taste profile, using at least a second element of biological extraction data as a function of two distinct taste profiles, wherein the second element of biological extraction data is more recent than the first element of biological extraction data; and offering at least a diagnosis to the user based on the change in the user taste profile.

10. The method of claim 9, wherein generating a taste profile further comprises:

classifying the user to a category of users as a function of a user classifier;

selecting a third training data matching the category of users; and training a taste classifier using the third selected training data.

11. The method of claim 9, wherein determining a change in user taste profile further comprises generating a second taste profile and determining the change in user taste profile as a function of the first taste profile and the second taste profile.

12. The method of claim 11, wherein generating the second taste profile further comprises receiving the second element of biological extraction.

13. The method of claim 12, wherein generating a taste profile further comprises:

calculating a second taste index as a function of the second element of biological extraction data; and generating the second taste profile as a function of the second taste index.

14. The method of claim 13, wherein determining a change in user taste profile further comprises calculating a difference between the first taste profile and the second taste profile.

15. The method of claim 14, wherein the change in user taste profile further comprises a correlation between at least a genetic element of a user and a taste measurement.

16. The method of claim 15, wherein the correlation further comprises a correlation determined using a classifier that limits training data for a machine learning process.

* * * * *